(12) United States Patent
Karst et al.

(10) Patent No.: US 10,765,857 B2
(45) Date of Patent: Sep. 8, 2020

(54) CUTANEOUS ELECTRODE DEVICE AND ELECTROSTIMULATION DEVICE INCLUDING SAID ELECTRODE DEVICE

(71) Applicant: COMMISSARIAT A L'ENERGIE ATOMIQUE ET AUX ENERGIES ALTERNATIVES, Paris (FR)

(72) Inventors: Nicolas Karst, Folkling (FR); Simon Perraud, Bandol (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 15/310,357

(22) PCT Filed: May 11, 2015

(86) PCT No.: PCT/IB2015/053457
§ 371 (c)(1),
(2) Date: Nov. 10, 2016

(87) PCT Pub. No.: WO2015/177677
PCT Pub. Date: Nov. 26, 2015

(65) Prior Publication Data
US 2017/0136229 A1    May 18, 2017

(30) Foreign Application Priority Data
May 19, 2014    (FR) .................................... 14 54462

(51) Int. Cl.
*A61N 1/36*    (2006.01)
*A61N 1/04*    (2006.01)

(52) U.S. Cl.
CPC ....... *A61N 1/0492* (2013.01); *A61N 1/36014* (2013.01); *A61N 1/36021* (2013.01)

(58) Field of Classification Search
CPC .......................... A61N 1/0492; A61N 1/36021
See application file for complete search history.

(56) References Cited

U.S. PATENT DOCUMENTS

| 2002/0038101 A1* | 3/2002 | Avrahami ............... A61N 1/30 |
| | | 604/20 |
| 2004/0088036 A1* | 5/2004 | Gilbert ................. A61H 39/002 |
| | | 607/148 |

(Continued)

FOREIGN PATENT DOCUMENTS

| AU | 740690 B2 | 11/2001 |
| FR | 2778108 A1 | 11/1995 |

OTHER PUBLICATIONS

Rapport de Recherche Preliminaire dated Sep. 5, 2014, issued in priority French Application No. 1454462, filed May 19, 2014, 1 page.

(Continued)

*Primary Examiner* — Rex R Holmes
(74) *Attorney, Agent, or Firm* — Christensen O'Connor Johnson Kindness PLLC

(57) ABSTRACT

A cutaneous electrode device intended for being connected to an electrical pulse generator including a planar body and an electrically insulating material on which at least one electrode, at least one means for connecting to the electrical pulse generator and at least one conductive element electrically connecting said electrode to said connection means are formed. The at least one electrode ends at an inner surface of the body and the at least one connection means ends at an outer surface of the body. The body also has at least one projecting portion that is mechanically connecting an electrode and a connection.

9 Claims, 5 Drawing Sheets

(56) References Cited

U.S. PATENT DOCUMENTS

| | | | | |
|---|---|---|---|---|
| 2009/0076559 A1* | 3/2009 | Libbus | ............... | A61N 1/046 607/6 |
| 2013/0023816 A1* | 1/2013 | Bachinski | ............ | A61N 1/044 604/20 |
| 2013/0060115 A1* | 3/2013 | Gehman | ............ | A61B 5/0416 600/372 |

OTHER PUBLICATIONS

International Search Report dated Sep. 9, 2015, issued in corresponding International Application No. PCT/IB2015/053457, filed May 11, 2015, 3 pages.
Written Opinion of the International Searching Authority dated Sep. 9, 2015, issued in corresponding International Application No. PCT/IB2015/053457, filed May 11, 2015, 5 pages.
Written Opinion of the International Searching Authority dated Sep. 9, 2015, issued in corresponding International Application No. PCT/IB2015/053457, filed May 11, 2015, 4 pages.
International Preliminary Report on Patentability dated Nov. 22, 2016, issued in corresponding International Application No. PCT/IB2015/053457, filed May 11, 2015, 1 page.

* cited by examiner

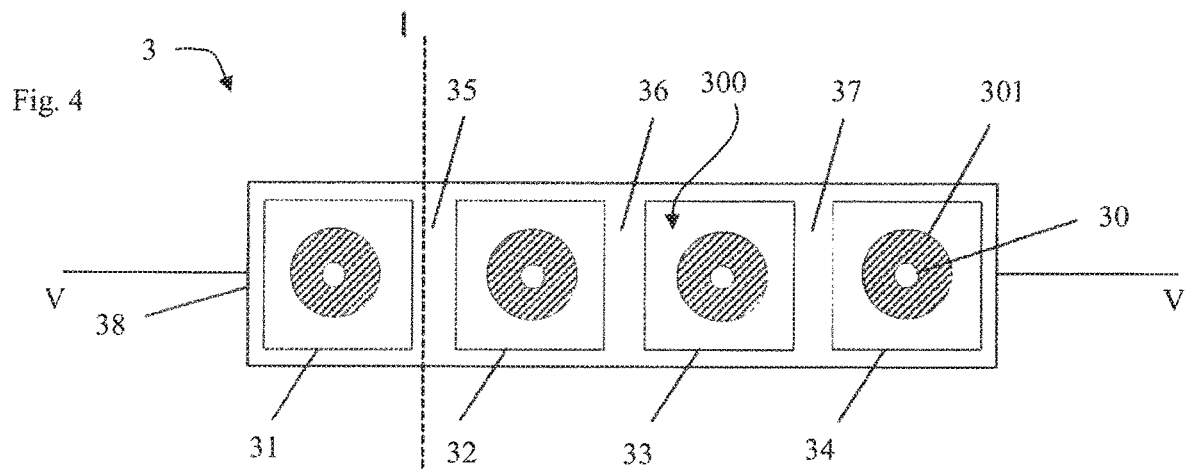
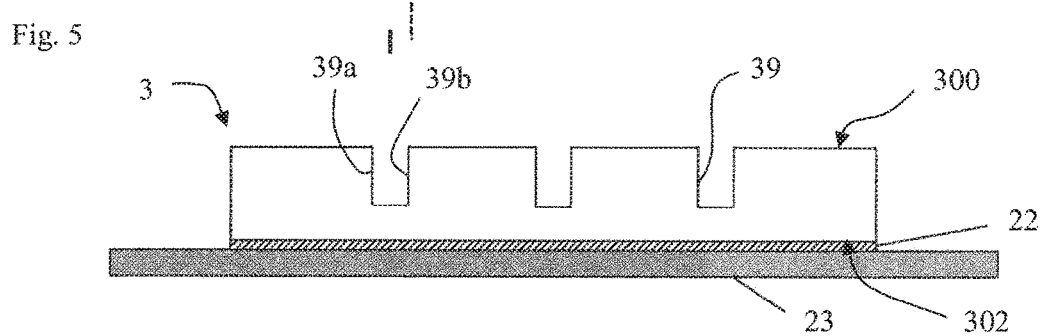
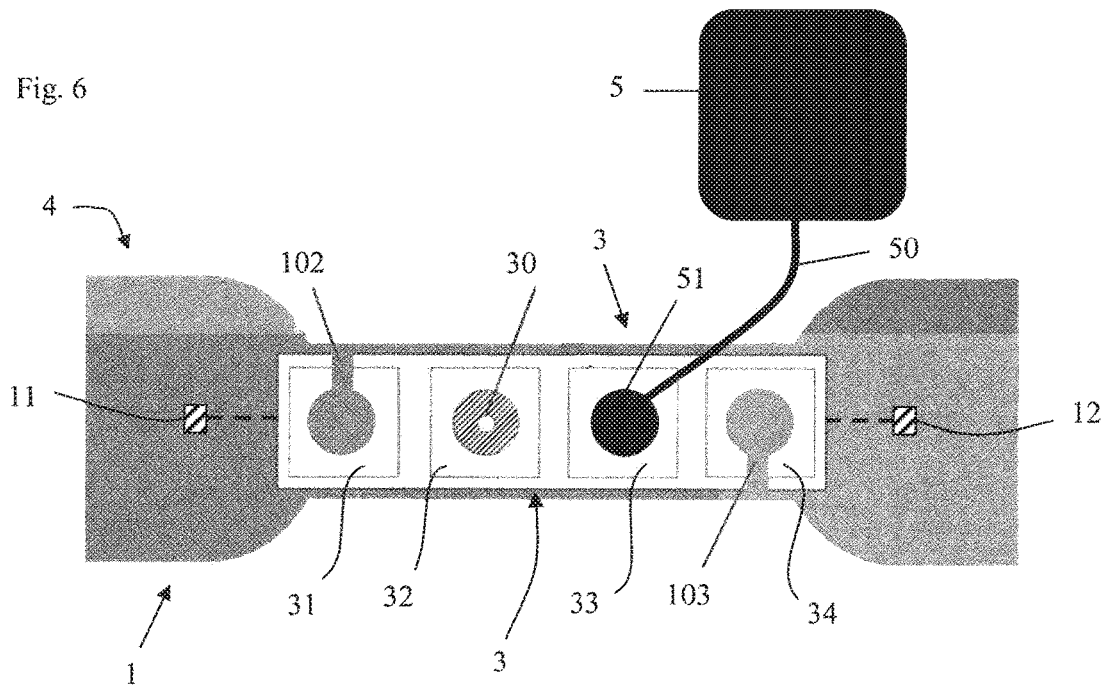

CUTANEOUS ELECTRODE DEVICE AND ELECTROSTIMULATION DEVICE INCLUDING SAID ELECTRODE DEVICE

This application is the National Stage of International Application No. PCT/IB2015/053457, filed May 11, 2015, which claims the benefit of French Application No. 1454462, filed May 19, 2014, all the disclosures of which are incorporated by reference therein.

The invention relates to the technical field of devices intended to be fixed on a user's skin.

It in particular relates to medical devices, such as cutaneous electrodes for measuring physiological parameters, cutaneous electrodes for electrostimulation, or pulse generators for electrostimulation.

In particular, conventional electrostimulation devices are made up of an electric pulse generator connected to cutaneous electrodes.

The electric pulse generator assumes the form of a bulky and rigid unit and makes it possible to send frequency- and intensity-calibrated electric pulses to a specific zone of the human body via cutaneous electrodes. To be able to be in contact with a multitude of stimulation zones, the cutaneous electrodes are connected to the unit via cables measuring several tens of centimeters.

Reference may be made to document U.S. Pat. No. 5,423,874, which describes a device of the patch type. It is maintained on the user's skin via a double-sided adhesive in which two openings have been formed beforehand such that the anode and the cathode can provide electrical contact with the user's skin. The anode and the cathode are also in contact with the pins of the electronic circuit. Another example of an electrostimulation device of the patch type is described in document WO 2013/106644. This electrostimulation device is made up of a pair of flexible electrodes incorporated at the lower surface of a rigid unit, within which the electrostimulation electronics are present.

The above devices (U.S. Pat. No. 5,423,874, WO 2013/106644) are kept in place on the patient's skin via adhesive electrodes. They have a fixed distance between the anode and the cathode, which also limits the addressable stimulation zones.

Thus, these electrostimulation devices are not versatile and can only be used for certain stimulation zones of the human body.

Patent application U.S. 2013/0158627 responds to some of the issues previously raised, but has the drawback of not being truly configurable in terms of use. Indeed, the choice of the electrically stimulated zone is determined and is not configurable.

The invention aims to offset these drawbacks by proposing an electrode device and electrostimulation device able to adapt to different zones of the human body to stimulate them.

Thus, the invention relates to a cutaneous electrode device intended to be connected to an electric pulse generator comprising a planar body made from an electrically insulating material on which at least one electrode, at least one means for connecting to the electric pulse generator and at least one conductive element electrically connecting said electrode to said connecting means are formed.

According to the invention, said at least one electrode emerges on an inner face of said body and said at least one connecting means emerges on an outer face of said body, said body including at least one protruding portion, said portion mechanically connecting an electrode and a connecting means and being intended to electrically and mechanically connect, by bending, said electrode device to said electric pulse generator.

Advantageously, the entire body is flexible.

At least part of this body preferably has an elongate shape, extending along the longitudinal axis, and includes at least two protruding portions. The latter may be arranged on either side of this axis.

This body includes at least one branch extending from the elongate part of said body while forming a non-zero angle with its longitudinal axis, an electrode being made on said at least one branch.

The electrode device may also comprise a grate formed on the inner face of said body and electrically connected to said at least one electrode.

In one alternative embodiment, the device also comprises at least one protruding portion complementary with a hole, this portion extending substantially along the same axis as said at least one portion and on the opposite side relative to said body.

The device advantageously comprises a layer of hydrogel, provided on said body at said at least one electrode.

The device may also comprise a double-sided adhesive on the zones of the body with no conductive elements.

The invention also relates to an electrostimulation device formed by the electrode device according to the invention and an electric pulse generator comprising at least one connecting means on its upper face, the lower face of said electric pulse generator being able to come into contact with the outer face of said electrode, and at least one protruding portion being capable of coming into contact with the upper face of the electric pulse generator by bending, and mechanically and electrically connecting it to said electrode device.

Advantageously, the electric pulse generator comprises at least two rigid zones electrically and mechanically connected by a flexible zone, these rigid zones bearing the components of the electric pulse generator as well as the means for connecting to electrodes.

Advantageously, this electrostimulation device includes magnetic means at the electrical connecting means provided on the electrode device or on the electric pulse generator.

This electrostimulation device advantageously includes at least one cutaneous electrode able to be electrically connected to said at least one connecting means of the electric pulse generator.

The invention will be better understood, and other aims, advantages and features thereof will appear more clearly, upon reading the following description done in reference to the appended drawings, in which.

Figure 1:
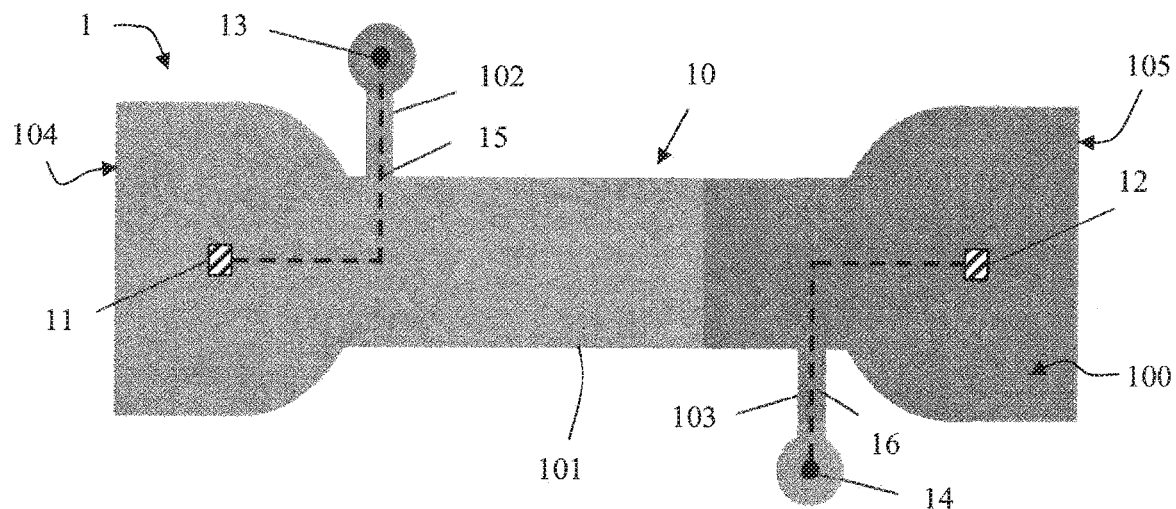
FIG. 1 is a top view of an electrode device according to the invention.
Figure 2:
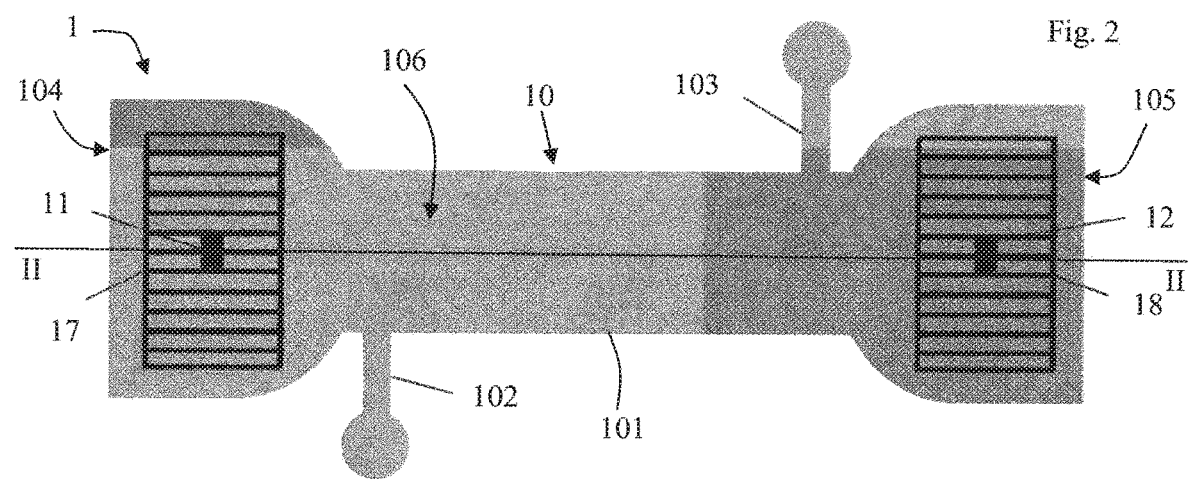
FIG. 2 is a bottom view of the electrode device illustrated in FIG. 1.
Figure 3:
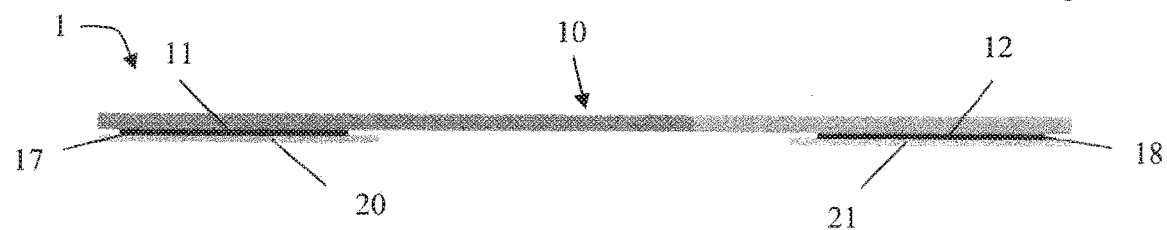
Figure 7:
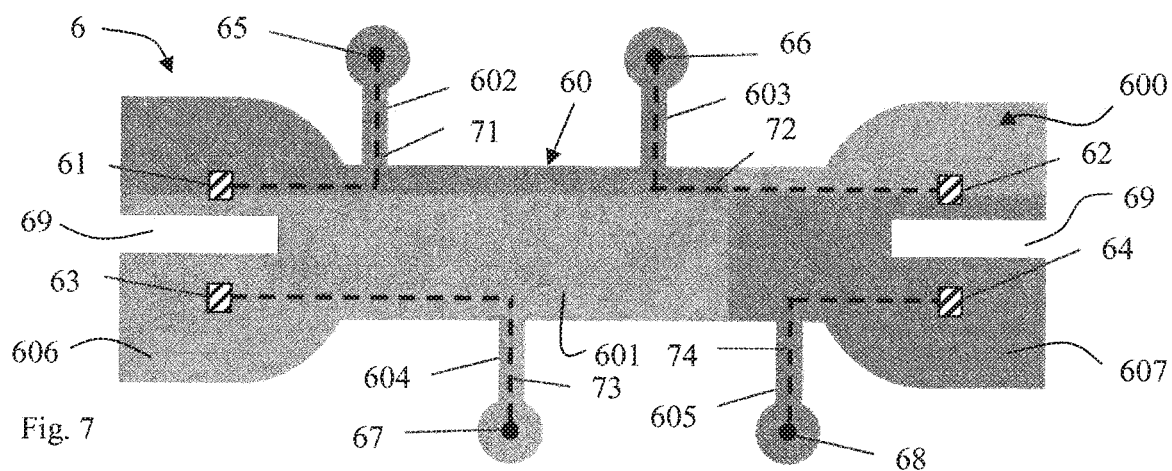
Figure 8:
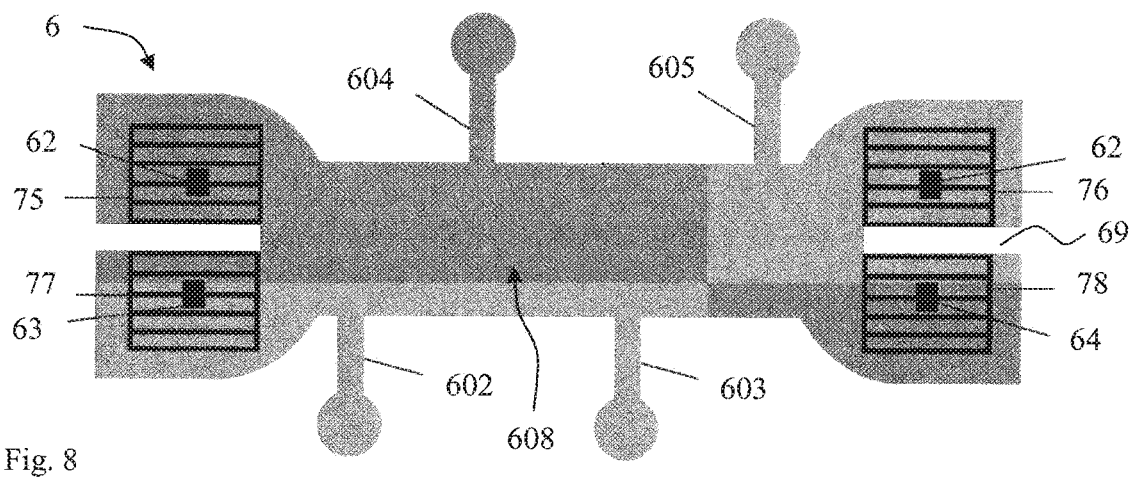
Figure 9:
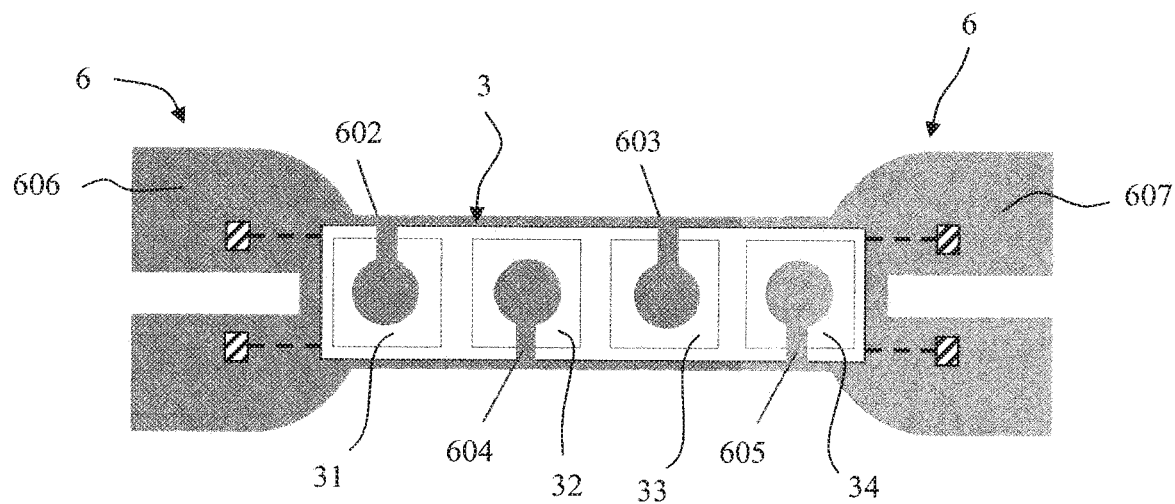
Figure 10:
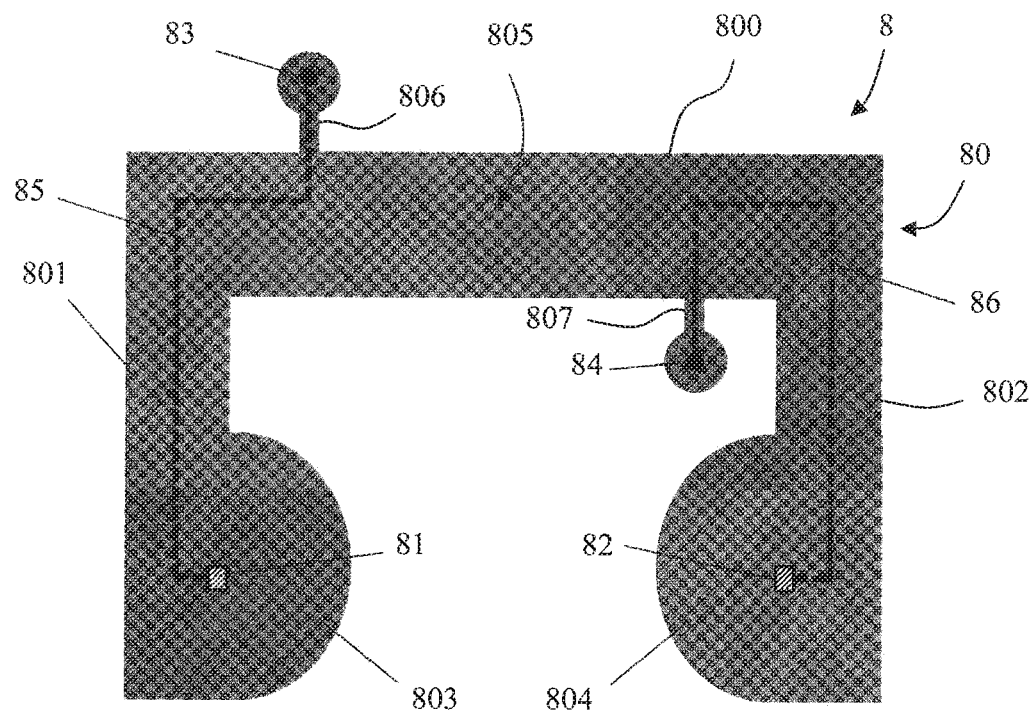
Figure 11:
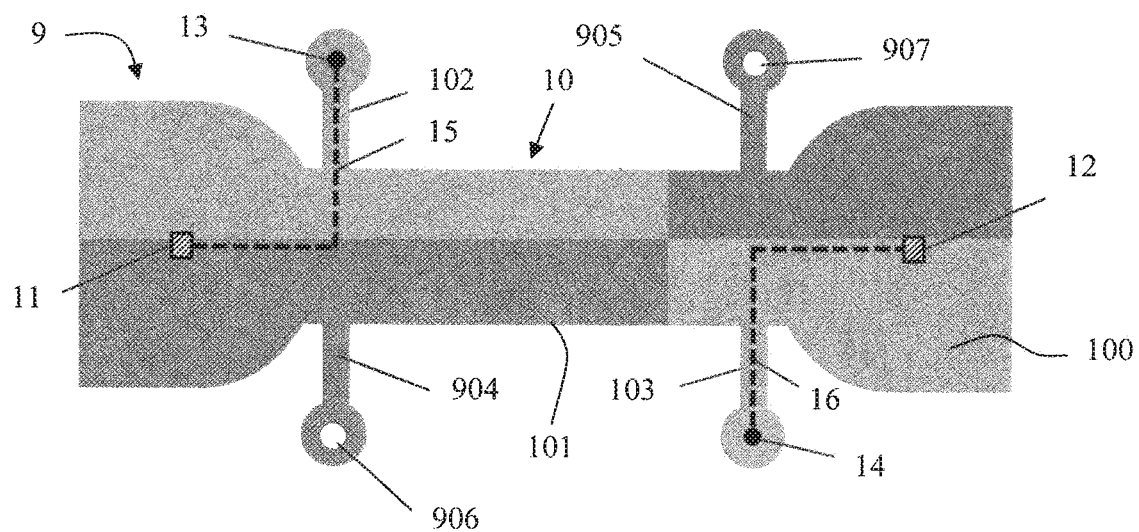

FIG. 3 is a sectional view along line II-II of the device illustrated in FIG. 2, FIG. 4 is a top view of an example electric pulse generator able to be associated with the electrode device illustrated in FIGS. 1 to 3, FIG. 5 is a sectional view along line V-V of FIG. 4, FIG. 6 is a top view of an assembly comprising an electrode device illustrated in FIGS. 1 to 3, and on which electric pulse generator according to FIGS. 4 and 5 is arranged, FIG. 7 is a top view of another example embodiment of an electrode device according to the invention, FIG. 8 is a bottom view of the electrode device illustrated in FIG. 7, FIG. 9 is a top view of an assembly comprising an electrode device according to FIGS. 7 and 8, on which an electric pulse generator according to FIGS. 4 and 5 is arranged, FIG. 10 is a top view of another example embodiment of the electrode device according to the invention, FIG. 11 is a top view of an alternative embodiment of the electrode device illustrated in FIGS. 1 to 3, and FIG. 12 is a top view of an assembly comprising an electrode device as illustrated in FIG. 11, on which electric pulse generator according to claims 4 and 5 is arranged.

The elements shared by the different figures will be designated using the same references.

FIG. 1 illustrates an electrode device 1 including a body 10 made from an electrically insulating material.

This body 10 will preferably be flexible and may in particular be made with a silicone base.

This body 10 is planar and includes a central part 101 with two protruding portions 102, 103 that protrude from this central part 101, as well as two side parts 104, 105 on either side of the central part 101.

In the example embodiment shown in FIGS. 1 and 2, the protruding portions each assume the form of a tongue.

According to one particular embodiment that is not shown, each protruding portion could assume the form of an elongated rebate extending along the body 10. In general, the protruding portions (tongues or rebates) may have different shapes from those illustrated in FIG. 1.

In the example illustrated in FIG. 1, the body 10 has an elongate shape that extends along the longitudinal axis. Furthermore, the protruding portions here are substantially perpendicular to the longitudinal axis and they extend in opposite directions.

In the body 10, two electrodes 11 and 12, two connecting means such as connecting plugs 13 and 14 and two conductive elements 15 and 16 are formed.

In order to provide an electrical connection with the connecting means of an electric pulse generator, the connecting plugs 13 and 14 emerge on an outer face 100 of the body 10. The outer face 100 is intended to come into contact with both a lower face and an upper face of the electric pulse generator, which will in particular be described in reference to FIGS. 4 and 5.

In order to provide an electrical connection with part of the human body, the two electrodes 11 and 12 emerge on an inner face 106 of the body 10, illustrated in FIG. 2. The inner face 106 is intended to come into contact with the human body (or with a hydrogel that will be in contact with the human body).

FIG. 1 shows that the connecting plugs 13 and 14, intended to provide the electrical connection between each electrode and the corresponding connecting means 30 of an electric pulse generator, are each arranged on a protruding portion 102, 103. They are preferably situated at the free end of these protruding portions.

Furthermore, the two conductive elements 15 and 16 are formed in the body 10. The first conductive element 15 allows an electrical connection of a first electrode 11 to a first connecting plug 13, while the second conductive element 16 makes it possible to electrically connect a second electrode 12 to a second connecting plug 14.

Furthermore, each electrode is mechanically connected to a connecting plug via a protruding portion.

The conductive elements 15 and 16 may assume the form of a simple electrically conductive cable or a conductive element of the metal track type, attached to the surface of the body 10 and the protruding portion 102 or 103.

For safety reasons, each conductive element 15 or 16 may be completely or partially encapsulated within the body 10 and the protruding portion 102 or 103. Likewise, the electrodes 11 and 12 present at the outer face 100 may be encapsulated within the body 10 at the outer face of the body and visible on its inner face. The connecting plugs 13 and 14 are designed so as to cooperate with the connecting means present on the electric pulse generator associated with the electrode device and an example of which is described in reference to FIGS. 4 and 5.

The protruding portions 102 and 103 may be arranged on either side of the body 10 as illustrated in FIG. 1, but could also be arranged on the same side, along the longitudinal axis of the body 10.

When the protruding portions 102 and 103 are arranged on either side of the body 10, the maintenance of the electric pulse generator can be improved, as will be described in reference to FIG. 6. Furthermore, in order to further improve the maintenance of the electric pulse generator, another embodiment of a cutaneous electrode device will be shown in FIGS. 11 and 12.

Reference is now made to FIGS. 2 and 3, which respectively show the inner face 106 of the electrode device 1 and a sectional view along line II-II.

These two figures illustrate a grate 17 or 18 that may be provided at the electrode 11 or 12, so as to diffuse the current homogenously at the user's skin.

The surface area occupied by each of the grates 17 or 18 will be comprised between 4 cm$^2$ and 150 cm$^2$, and preferably equal to 50 cm$^2$. The surface area occupied by the grate will advantageously be greater than 5% of the surface area of the body 10.

Furthermore, in order to improve the transfer of the current between the electrodes 11 or 12 and the user's skin, a layer of hydrogel 20 or 21 can be added. This layer of hydrogel 20 or 21 can, in addition to its current conducting property, have an adhesion property (adhesion both on the electrode device 1 and on the skin).

In order to reinforce the maintenance of the electrode device 1 on the user's skin, an adhesive may be provided on the inner face 106 of the body 10, opposite the face 100. Other fastening means may be provided, such as a bracelet, leg warmer, armband or belt.

The invention is not limited to this embodiment. In particular, the body 10 could include only one electrode or a plurality of electrodes.

Reference is now made to FIGS. 4 and 5, which illustrate an example electric pulse generator that can be used in combination with the electrode device described in reference to FIGS. 1 to 3 to form an electrostimulation device.

The electric pulse generator 3 here has a rectangular shape and has one or several flexure axes parallel to the axis I-I. In the example illustrated in FIG. 3, the electric pulse generator 3 is made up of four rigid zones 31, 32, 33, 34 electrically and mechanically connected by three flexible zones 35, 36, 37 extending along the axis I-I or an axis parallel to the axis I-I.

More generally, the electric pulse generator 3 may be made up of at least two rigid zones electrically and mechanically connected by at least one flexible zone, allowing flexure along at least part of an axis parallel to the axis I-I.

Each of the rigid zones makes it possible to accommodate one or several components of the electric pulse generator 3. It will for example be possible to arrange the electrostimulation electronics on the rigid zone 31 and three batteries on the rigid zones 32, 33 and 34.

This example electric pulse generator is flexible. In other example embodiments, the electric pulse generator could be flexible over its entire surface, as long as all of the elements making up the electric pulse generator are also flexible.

In order to protect the electronic components and the batteries from the outside environment, they are advantageously encapsulated by a coating 38. This coating 38 may be a silicone overmolded element marrying the specific shapes of the electric pulse generator.

The thickness of this element 38 will be comprised between 0.2 mm and 5 mm. It may be present both on the top and bottom of the electric pulse generator 3. This coating 38 may partially or completely cover the rigid elements and the flexible elements. The surface are of this coating 38 may be larger than the cumulative surface areas of the flexible elements and rigid elements.

As shown in FIG. 5, the electric pulse generator 3 may have recesses 39 in order to improve flexibility.

The depth of the recesses will preferably be greater than 50% of the total thickness of the electric pulse generator 3.

A connecting means 30 is provided on each of the rigid zones 31, 32, 33 and 34, this connecting means 30 making it possible to electrically connect a cutaneous electrode to the electric pulse generator.

In one advantageous embodiment of the generator 3, each of the electric connecting means 30 may be designed to define a rigid zone of the generator and thus to provide effective mechanical protection for the components present in this zone.

Thus, the generator can comprise two successive layers, i.e., a first layer comprising the electric connecting means and a second layer comprising the flexure-sensitive components.

Each of the electric connecting means then has, in the plane of the device, a surface area corresponding to at least one component and is arranged so as to cover this component. It thus defines a rigid zone in which the mechanical protection of this component is ensured.

In order to ensure the mechanical protection of all of the components present in a portion of the generator 3, each of the connecting means has, in the plane of the device, a surface area larger than that occupied by these components and is aligned with them along the thickness of this portion of the generator, so as to cover them.

Owing to this embodiment, it is not necessary to provide a rigid unit to protect the components from mechanical stresses.

Furthermore, to the extent that the flexure-sensitive components can be present in the flexible zones 35, 36, 37, the generator 3 can also comprise means for limiting the flexure to limit or block the flexure of these flexible zones relative to an axis parallel to the axis I-I.

In the example shown in FIG. 5, the opposite walls 39a and 39b of two adjacent rigid zones can constitute means for limiting the flexure relative to an axis parallel to the axis I-I, when the flexure tends to bring these opposite walls closer to one another.

The connecting means 30 are situated on the upper face 300 of the electric pulse generator 3 and here assume the form of holes.

If the connecting means 30 are holes, the connecting plugs of the electrode device 1 may be partially metal elements having a protruding part making it possible to cooperate with these connecting means 30. The cooperation between the electrode device and the electric pulse generator 3 is described in reference to FIG. 6.

Furthermore, different connecting means can be considered to electrically connect an electrode to the electric pulse generator. These means can comprise a plug electrically connected to the electrode via a cable, the plug being designed to cooperate with at least one connecting means present on the electric pulse generator, so as to electrically connect this plug to the electronic circuit of the electric pulse generator.

For example, the plug and the connecting means can form a system of the pushbutton type already used in some conventional electrostimulation devices to connect the cables from the unit to the cutaneous electrodes.

On the electric pulse generator 3 illustrated in FIG. 4, it is possible to simultaneously connect up to four cutaneous electrodes via four connecting means 30.

The coating 38 will have openings at the holes 30, so that the plugs can be electrically connected to the electronic circuit.

In order to facilitate the connection of the cutaneous electrodes via plugs, magnetic elements may be integrated at the connecting means 30 of the electric pulse generator 3 and the plugs.

These magnetic elements are intended to exert an attractive magnetic force on one another. Thus, it suffices for a plug to be close to a connecting means for the magnetic forces to become active and the connection between the plug and the connecting means to be produced.

In the example illustrated in FIG. 4, magnetic elements 301 are integrated at the electric pulse generator.

The elements 301 can be magnets with a base of neodyme, iron and boron.

The elements 301 may be covered with the coating 38.

In order to keep the electric pulse generator 3 on the user's skin, a double-sided adhesive 22 can be used as illustrated in FIG. 5. One face of the adhesive 22 is then in contact with the lower face 302 of the electric pulse generator 3, another face of the adhesive 22 being in contact with the user's skin 23. Thus, the lower face 302 of the electric pulse generator 3, opposite the upper face 300, is intended to be opposite the user's skin.

However, the electric pulse generator described in FIGS. 4 and 5 is preferably used with the electrode device described in reference to FIGS. 1 to 3.

Reference is now made to FIG. 6, which illustrates the placement of the electric pulse generator 3 on the electrode device 1.

FIG. 6 shows that the electric pulse generator 3 is arranged on the central part 101 of the body 10 and on the outer face 100 of said body 10, on which face the connecting plugs 13 and 14 emerge. The lower face 302 of the electric pulse generator 3 is thus in contact with the outer face 100 of the body 10 of the electrode device, at its central part 101.

FIG. 6 shows that after the placement of the electric pulse generator 3, the protruding portions 102 and 103 are bent on the upper face of the electric pulse generator 3 such that the connecting plugs 13 and 14 are electrically connected to a connecting means 30. Thus, part of the outer face 100 of the body 10, situated at the protruding portions 102 and 103, is in contact with the upper face 300 of the electric pulse generator 3.

The electrical connection of one of the electrodes 11 and 12 of the electrode device 1 and the connecting means 30 of the electric pulse generator 3 is therefore done on the upper face 300 of the electric pulse generator 3. This configuration makes it possible to connect other cutaneous electrodes on the electrostimulation device formed by the device 1 and the electric pulse generator 3, as will be described later, and contributes to the versatility of the assembly.

Thus, once the connecting plugs 13 and 14 are connected, the protruding portions 102 and 103 make it possible, in addition to the electrical connection, to jointly and removably maintain the electric pulse generator 3 at the electrode device to form an electrostimulation device.

The obtained electrostimulation device 4 is next applied on the patient's skin and is kept in place owing to the hydrogel layers 20 and 21 present at the electrodes 11 and 12 and/or owing to the double-sided adhesive 22.

Thus, owing to the configuration of the invention, the upper face and in particular the connecting means 30 of the electric pulse generator are accessible.

It is then also possible to connect an additional cutaneous electrode at the connecting means 30 of the rigid zones 32 and 33. Such an electrode 5 is illustrated in FIG. 6, connected to the zone 33 via the cable 50 and the connecting means 51.

It should be noted that it is possible for at least one of the connecting means 13 or 14 not to be electrically connected to the connecting means 30 present on the electric pulse generator. In this case, the tongue(s) 102 and/or 103 only provide the mechanical maintenance of the electric pulse generator 3 on the electrode device 1.

Owing to the electrode device, the electric pulse generator 3 may be used to treat pathologies such as lumbar pain, by placing it at the lower back.

Furthermore, due to the specific architecture of the electrostimulation device (patch), it is possible, as previously mentioned, to couple the electrode device with two other cutaneous electrodes thus making it possible, with a same electrostimulation device, to simultaneously perform antalgic stimulations (instantaneously inhibiting pain), delivered via the electrode device 1, and and/or endorphin stimulations (prolonging the absence of painful sensations due to endorphin production), delivered via cutaneous electrodes 5.

Lastly, once removed from the electrode device, the electric pulse generator 3 may be used to treat other places on the human body, in particular by using cutaneous electrodes 5 as shown in FIG. 6.

Thus, owing to the electrode device, the electrostimulation device according to the invention has the versatility allowing it to be used by patients with varied pathologies, as well as by patients with multiple pathologies. It is also possible to consider the simultaneous use of several electric pulse generators in different locations of the human body.

The electrode device according to the invention may adapt to other forms of electric pulse generators than the one described in reference to FIGS. 4 and 5.

The surface area occupied by the electrode device will preferably be at least equal to the surface area occupied by the electric pulse generator 3.

Different sizes or shapes of the electrode device may be considered, based on the zones to be stimulated or the morphology of the people using the electrostimulation device.

Reference is now made to FIGS. 7 to 9, which illustrate an alternative embodiment of the electrode device according to the invention.

In this alternative embodiment, four protruding portions 602, 603, 604 and 605 extend, here in the form of a tongue, from the central part 601 of the body 60.

The body 60 includes, on either side of the central part 601, two side parts 606 and 607.

FIG. 7 shows that the tongues 602 and 603 extend on the same side of the longitudinal axis along which the body 60 extends, while the tongues 604 and 605 extend on the other side of this axis relative to the tongues 602 and 603.

In the example illustrated in FIGS. 7 to 9, these tongues extend substantially perpendicular to the longitudinal axis of the body 60.

Furthermore, the tongues 602 to 605 are arranged alternating on either side of the central part 601 of the body 60. The interest of this arrangement will be illustrated by FIG. 8.

Four electrodes 61, 62, 63 and 64, four connecting plugs 65, 66, 67 and 68 and conductive elements 71, 72, 73 and 74 are made in the body 60.

In order to ensure an electrical connection with the connecting means 30 of an electric pulse generator 3, the connecting plugs 65, 66, 67 and 68 emerge on an outer face 600 of the body 60. The outer face 600 is intended to come into contact with the lower face 302 of the electric pulse generator 3, at the central part of the body 60.

In order to ensure an electrical connection with a part of the human body, the four electrodes 61, 62, 63 and 64 emerge on an inner face 608 of the body 60. This face 608 is opposite the outer face 600 and is intended to come into contact with the human body.

These conductive elements 71 to 74 make it possible to electrically connect each electrode 61 to 64 to the connecting means 65 to 68, preferably connecting plugs.

Furthermore, each electrode is mechanically connected to a connecting plug via a tongue.

Each of these tongues is preferably flexible.

In the example illustrated in FIG. 7, the conductive elements 71 to 74 assume the form of a metal track formed on the outer face 600 of the body 60.

In another embodiment, these conductive elements could assume the form of an electrically conductive cable.

As described in reference to FIG. 1, for safety reasons, the conductive elements 61 to 64 may be completely or partially encapsulated within the body 60 and each of the tongues 602 to 605.

The connecting means 65 to 68 are designed so as to cooperate with the connecting means present on an electric pulse generator like that illustrated in FIGS. 4 and 5.

A grate 75, 76, 77, 78 can be provided on the inner face 608 of the body 10 opposite the outer face 600 and at the electrode 61, 62, 63 or 64, in order to diffuse the current homogenously at the user's skin.

The surface area occupied by each of the grates 75 to 78 will be comprised between 4 cm$^2$ and 150 cm$^2$, and preferably equal to 50 cm$^2$.

Likewise, in order to improve the transfer of the current between the electrodes 61 to 64 and the user's skin, a hydrogel layer may be added (not shown in the figures).

It is also possible to consider using four separate hydrogel-based elements, each hydrogel element being placed across from one of the grates 75 to 78, to improve the transfer of the current between the electrodes and the user's skin.

In light of the high lateral resistivity of the hydrogel elements, it is also possible to consider using only two hydrogel elements, one being across from the grates 75 and 76, the other being across from the grates 77 and 78.

In order to reinforce the maintenance of the electric pulse generator 3 on the skin, it is possible to add an adhesive on the rear face of the central part of the body 60.

The body 60 of the electrode device 6 has a recess 69 in each lateral part 606, 607 of the body 60, so as to improve the conformability of the electrode device. Other forms of this body 60 may also be considered.

Reference is now made to FIG. 9, which illustrates the electric pulse generator 3 after it has been placed on the electrode device 6.

This placement is done as previously described in reference to FIG. 6, for the electrode device 4.

FIG. 9 shows that after the placement of the electric pulse generator 3, the protruding portions 602, 603, 604 and 605 are bent on the upper face 300 of the electric pulse generator 3, such that the connecting plugs 65, 66, 67 and 68 are electrically connected to the connecting means 30. Thus, part of the outer face 600 of the body 60, situated at the protruding portions 602, 603, 604 and 605, is in contact with the upper face 300 of the electric pulse generator 3.

FIG. 9 shows that the connecting means 65 to 68 are electrically connected to the connecting means 30 of each of the rigid zones 31 to 34 of the electric pulse generator 3, owing to the bending of each of the tongues 602 to 605.

Thus, once the connecting plugs 65, 66, 67 and 68 are connected, the protruding portions 602, 603, 604 and 605 make it possible, in addition to the electrical connection, to securely and removably fasten the electric pulse generator 3 to the electrode device.

One or several connecting means 65 to 68 may not be electrically connected to the connecting means 30 present on the electric pulse generator. Thus, the tongues having such connecting plugs merely provide mechanical maintenance.

Reference is now made to FIG. 10, which illustrates an alternative embodiment of the electrode device according to the invention.

In the alternative embodiment, the device 8 includes a body 80 that is substantially U-shaped, with a central part 800 forming the base of the U extending along a longitudinal axis and two branches 801 and 802, extending substantially perpendicular to the longitudinal axis.

It is also possible to consider other embodiments in which the two branches extend in opposite directions, the body includes only one branch extending from the central part of the body, or the branch or branches extend in a direction forming a non-zero angle smaller than 90° with the longitudinal axis of the central part.

The two branches 801 and 802 include, at their ends, a wider part 803 and 804.

Two electrodes 81 and 82, two connecting means such as connecting plugs 83 and 84 as well as two conductive elements 85 and 86 are formed in the body 80.

In order to provide electrical connection with, for example, the connecting means 30 of the electric pulse generator illustrated in FIGS. 4 and 5, the connecting plugs 83 and 84 emerge on an outer face 805 of the body 80.

Furthermore, in order to provide an electrical connection with part of the human body, the two electrodes 81 and 82 emerge on an inner face of the body 80, opposite the outer face 805. This inner face is intended to come into contact with part of the human body (or with a hydrogel that will be in contact with the human body).

The two conductive elements 85 and 86 are formed in the body 80; the first conductive element 85 makes it possible to electrically connect the first electrode 81 to the first connecting plug 83, while the second conductive element 86 makes it possible to electrically connect the second electrode 82 to the second connecting plug 84.

The connecting plugs 83 and 84 are arranged on protruding portions 806 and 807 that each extend from the base 800 of the body 80.

These two protruding portions 806 and 807 extend in opposite directions, relative to the base 800 of the body 80.

As previously explained, in particular in light of FIGS. 6 and 9, an electric pulse generator 3 can be associated with the electrode device 8, such that its lower face 302 comes into contact with the outer face 805 of the device 8, at its base 800.

Furthermore, at the connecting plugs 83 and 84, the outer face of the device 8 comes into contact with the upper face 300 of the generator.

The electric pulse generator can thus be maintained securely and yet removably on the electrode device 8.

The particular form of the body 8 makes it possible to separate the electrodes 81 and 82 from the electric pulse generator 3. This separation depends on the length of the branches 801 and 802 of the body 80. The branches are situated on the same side or on either side of the body 80.

This electrode device may advantageously be used to treat painful zones at a joint, and in particular at the knee.

Figure 12:
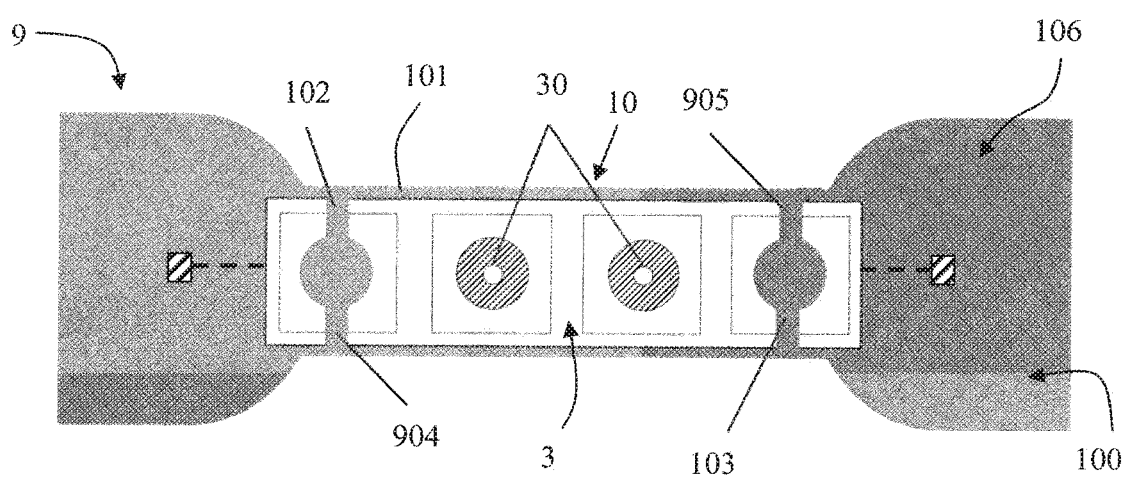

Reference is now made to FIGS. 11 and 12, which illustrate an alternative embodiment of the electrode device previously described in reference to FIGS. 1 to 3.

This electrode device 9 includes the same elements as the device 1 illustrated in FIGS. 1 to 3. These elements will not be described again.

This device 9 also includes two complementary protruding parts 904 and 905 that are situated opposite a protruding portion 102, 103, relative to the central part 101 of the body 10.

Thus, the protruding portion 904 extends substantially along the same axis as the protruding portion 102, but in an opposite direction relative to the central part 101. The same is true for the protruding portion 905 relative to the protruding portion 103.

Each of these protruding portions 904, 905 has a through hole 906, 907, the function of which will now be explained in light of FIG. 12.

This FIG. 12 illustrates the placement of the electric pulse generator 3 on the electrode device 9.

As explained in light of FIG. 6, the electric pulse generator 3 is arranged on the central part 101 of the body 10 and in contact with the outer face 101 of this body 10.

After the placement of the generator 3, the complementary protruding portions 904 and 905 are bent on the upper face of the electric pulse generator 3, while aligning the holes 906 and 907 with the connecting means 30 of the generator 3.

The protruding portions 102 and 103 are, secondly, also bent on the upper face of the generator 3, such that the connecting plugs 13 and 14 are electrically connected to a connecting means 30.

Thus, the connecting plugs 13 and 14 pass through holes 906 and 907 to provide the electrical connection with the connecting means 30.

This alternative embodiment makes it possible to improve the mechanical maintenance of the electric pulse generator 3 on the electrode device 9, owing to the presence of complementary protruding portions 904 and 905.

The preceding description shows that, owing to the electrode device according to the invention, an electrostimulation device can be adapted to different zones of the human body, without modifying its structure.

The reference signs inserted after the technical features appearing in the claims are intended solely to facilitate the understanding of the latter and cannot limit their scope.

The invention claimed is:

1. A cutaneous electrode device configured to be connected to an electric pulse generator, the device comprising:

a planar body having an inner face configured for contacting human body, and an outer face facing away from the inner face, wherein the planar body is made from an electrically insulating material on which are formed:
at least one electrode,
at least one connecting means to the electric pulse generator, and
at least one conductive element electrically connecting said electrode to said connecting means,
wherein the at least one electrode is situated on the inner face of the body and the at least one of the connecting means in operation emerges on the outer face of the body, and wherein the body includes at least one protruding portion that extends parallel to the inner face and the outer face, and laterally away from the body, and wherein the protruding portion mechanically connects an electrode and the connecting means, and
wherein the connecting means are configured to electrically and mechanically connect, by bending the at least one protruding portion, the electrode device to the electric pulse generator,
wherein at least part of the body has an elongate shape, extending along a longitudinal axis, and including at least two protruding portions and wherein the at least two protruding portions are arranged on either side of the longitudinal axis.

2. The device of claim 1, wherein the entire body is flexible.

3. The device of claim 1, wherein the body includes at least one branch extending from the elongate part of the body and forming a non-zero angle with the longitudinal axis, wherein the at least one branch carries the at least one electrode.

4. The device of claim 1, further comprising a grate formed on the inner face of the body and electrically connected to the at least one electrode.

5. The device of claim 1, wherein the at least one protruding portion is a first protruding portion, the device further comprising at least one second protruding portion complementary with a hole, the second protruding portion extending substantially along the same axis as the first protruding portion and on the opposite side relative to the body.

6. An electrostimulation device formed by a cutaneous electrode device according to claim 1, further comprising the electric pulse generator having an upper face and a lower face facing opposite from the upper face, the electric pulse generator having at least one connecting means on the upper face, wherein the lower face of the electric pulse generator is configured to come into contact with the outer face of the electrode, and wherein at least one protruding portion is capable of coming into parallel contact with the upper face of the electric pulse generator by bending to mechanically and electrically connect the electric pulse generator to the electrode device, wherein, prior to bending to mechanically and electrically connect the electric pulse generator to the electrode device, the protruding portion extends parallel to the upper face and the lower face, and laterally away from the body.

7. The electrostimulation device of claim 6, wherein the electric pulse generator comprises at least two rigid zones electrically and mechanically connected by a flexible zone, wherein the rigid zones carry components of the electric pulse generator and means for connecting to the individual electrodes.

8. The electrostimulation device of claim 6, including magnetic means at the electrical connecting means provided on of the cutaneous electrode device or of the electric pulse generator.

9. The electrostimulation device of claim 6, further comprising a cutaneous electrode electrically connected to the at least one connecting means of the electric pulse generator.

* * * * *